United States Patent
Ha et al.

(10) Patent No.: US 8,471,214 B2
(45) Date of Patent: Jun. 25, 2013

(54) METHOD FOR PROCESSING 3D DISTRIBUTION IMAGE OF RADIATION SOURCE AND SYSTEM USING THE SAME

(75) Inventors: Jang Ho Ha, Daejeon (KR); Han Soo Kim, Chungchungnam-do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 43 days.

(21) Appl. No.: 13/301,855

(22) Filed: Nov. 22, 2011

(65) Prior Publication Data

US 2012/0168636 A1    Jul. 5, 2012

(30) Foreign Application Priority Data

Dec. 30, 2010  (KR) .................. 10-2010-0138959

(51) Int. Cl.
*G01J 1/42*    (2006.01)

(52) U.S. Cl.
USPC ........................................................ 250/394

(58) Field of Classification Search
USPC ..................... 250/394, 362, 363.01–363.1
See application file for complete search history.

(56) References Cited

U.S. PATENT DOCUMENTS

| | | | |
|---|---|---|---|
| 6,177,675 B1 * | 1/2001 | Gagnon et al. | 250/363.1 |
| 7,321,122 B2 | 1/2008 | Bryman | |
| 7,917,192 B2 * | 3/2011 | Dos Santos Varela | 600/431 |
| 7,999,235 B2 | 8/2011 | Kohara et al. | |

FOREIGN PATENT DOCUMENTS

| | | |
|---|---|---|
| CA | 2230470 A1 | 3/1997 |
| JP | 2008514952 A | 5/2008 |
| JP | 2008522168 A | 6/2008 |
| KR | 100948461 B1 | 3/2010 |
| WO | 2006049523 A2 | 5/2006 |
| WO | 2006058432 A1 | 6/2006 |
| WO | 2008035708 A1 | 3/2008 |
| WO | 2012077468 A1 | 6/2012 |

OTHER PUBLICATIONS

Douraghy et al., "FPGA electronics for OPET: A dual-modality optical and positron emission tomograph," 2008, IEEE Transactions on Nuclear Science vol. 55, No. 5, pp. 2541-2545.*

* cited by examiner

*Primary Examiner* — Kiho Kim
(74) *Attorney, Agent, or Firm* — Fredrikson & Byron, PA

(57) ABSTRACT

A system for processing three dimensional (3D) distribution image of a radiation source and a processing method using the same are provided. The system includes an image measuring unit comprising a plurality of position sensitive detectors to measure the radiation source, a signal amplifying unit which receives signals from the image measuring unit and amplifies the received signals into an electric signal, a mode selecting unit that receives the electric signal and selects a detection mode and outputs a corresponding mode signal, a data storage unit which stores the signals as a series of items, a data converting unit which converts the data stored at the data storage unit into interactive data, an image reconstructing unit which reconstructs the converted data into the 3D distribution image, and a display unit which displays the 3D distribution image received from the reconstructing unit.

10 Claims, 2 Drawing Sheets

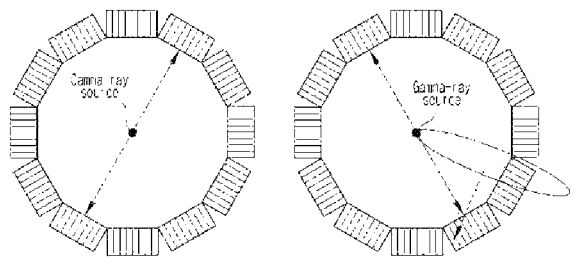
Fig. 3A  Fig. 3C
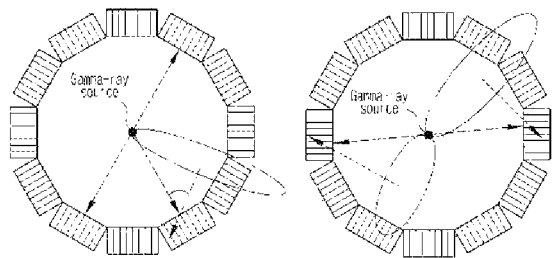
Fig. 3B  Fig. 3D
Fig. 4
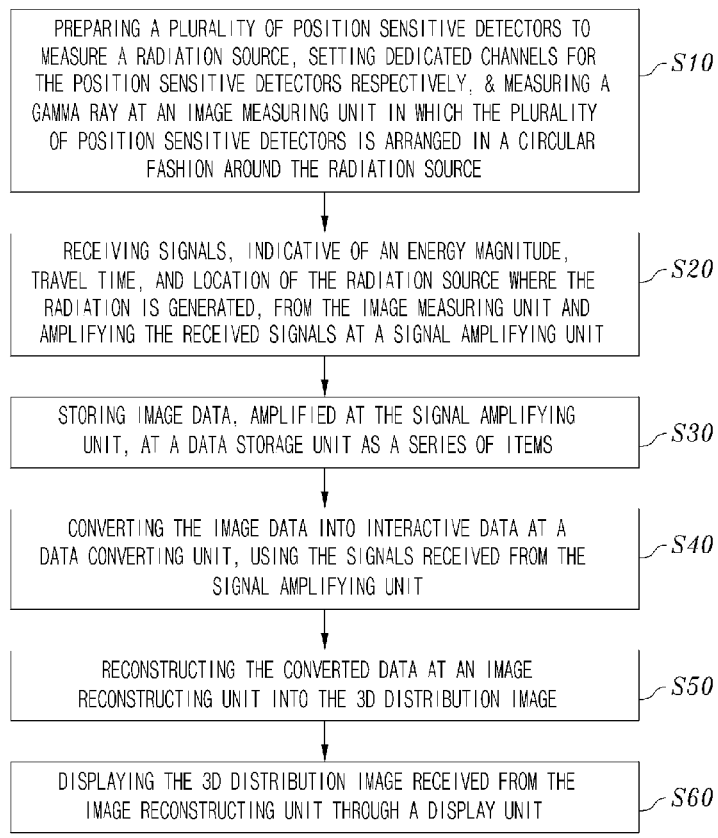

METHOD FOR PROCESSING 3D DISTRIBUTION IMAGE OF RADIATION SOURCE AND SYSTEM USING THE SAME

CROSS-REFERENCES TO RELATED APPLICATIONS

This patent application claims the benefit of priority from Korean Patent Application No. 10-2010-0138959, filed on Dec. 30, 2010, the contents of which are incorporated herein by reference in its entirety.

BACKGROUND OF THE INVENTION

1. Field of the Invention

The invention relates to a radiological imaging apparatus, and more particularly, to a method for processing 3-dimensional (3D) distribution image of radiation source to acquire 3D distribution of radiological image with improved sensitivity and image resolution, and a system using the same.

2. Description of the Related Art

The invention relates to a position sensitive detector-based imaging apparatus which acquires a three dimensional (3D) distribution image of a radiation source existing within a living organism. The single-photon emission computed tomography (SPECT) and positron emission tomography (PET) are the two representative examples of a conventional radiological imaging apparatus. SPECT uses a mechanical collimator which is made from materials such as lead or tungsten to acquire image from the radiation source.

However, the gamma ray sensitivity and the image resolution are in inverse relationship with each other, according to the aperture size of the collimator.

That is, if the sensitivity increases, the resolution degrades, and if the resolution improves, then the sensitivity decreases. There also is a drawback related to the use of mechanical collimator. That is, SPECT imaging equipment has increased size to accommodate the mechanical collimator, and has to be rotated to acquire 3D image.

PET concurrently receives 511 keV gamma rays emanating from the radiation source to acquire images of the radiation source distributed within the matter. Unlike SPECT, PET does not have to be rotated due to the circular arrangement of detectors. However, since PET uses higher magnitude of gamma ray energy than SPECT, PET has more Compton scattering due to photoelectric effect of the gamma rays at the detectors, rather than the entire energy is absorbed.

Due to the multi-scattering of gamma rays inside the respective detectors, the gamma rays are measured concurrently through a plurality of channels. Since the radiation source is not always present at the center of the imaging apparatus, the gamma rays can enter the apparatus through not only the surface of incidence, but also the side of the apparatus.

However, the above causes inaccuracy of position measurement. Such event works as a background event that obscures the image of the imaging apparatus such as PET. Due to the above-mentioned limits, the conventional imaging apparatus including PET has image resolution which is limited within a range of several mm at the maximum.

SUMMARY OF THE INVENTION

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

An object of the present invention is to provide a method for processing a three-dimensional (3D) distribution image of a radiation source and a system using the same, which are capable of resolving limited sensitivity and image resolution which are generated due to structural limits of a conventional radiological imaging apparatus, by utilizing all the methods that involve interaction between gamma rays and detectors.

In one embodiment, a system for processing three dimensional (3D) distribution image of a radiation source may be provided, which may include an image measuring unit which comprises a plurality of position sensitive detectors to measure the radiation source, the plurality of position sensitive detectors each having a devoted channel set therefore, and being arranged in a circularly fashion around the radiation source, a signal amplifying unit which receives signals indicative of energy magnitude and location of the radiation source from the image measuring unit and amplifies the received signals into an electric signal, a mode selecting unit which receives the electric signal generated at the signal amplifying unit, and selects a detection mode according to the energy magnitude and the location and outputs a corresponding mode signal, a data storage unit which stores the signals indicative of the energy magnitude, time of radiation generation, and location of the radiation source, and the signal received from the mode selecting unit as a series of items, a data converting unit which converts the data stored at the data storage unit into interactive data, an image reconstructing unit which reconstructs the converted data into the 3D distribution image, and a display unit which displays the 3D distribution image received from the reconstructing unit.

The image measuring unit may include the plurality of position sensitive detectors in N×M size (N, M=natural number), and the plurality of position sensitive detectors each detect the location of the radiation source, travel time and energy magnitude of the radiation through channels different from each other.

The plurality of position sensitive detectors each comprise a plurality of signal electrodes of a predetermined shape with width (k) and height (k).

The mode selecting unit categorizes the electric signal received along the respective channels to under coincidence mode.

The mode selecting unit categorizes the electric signal received along the respective channels to under single tracking mode of dual gamma ray.

The mode selecting unit categorizes the electric signal received along the respective channels to under coincidence mode/gamma ray tracking mode.

The mode selecting unit categorizes the electric signal received along the respective channels to under coincidence dual gamma ray tracking mode.

The mode selecting unit implements the coincidence mode, single tracking mode of dual gamma rays, coincidence mode/gamma ray tracking mode, and coincidence dual gamma ray tracking mode, depending on the electric signal received through the respective channels.

In one embodiment, a system for processing three dimensional (3D) distribution image of a radiation source may be provided, which may include an image measuring unit which comprises a plurality of position sensitive detectors to measure the radiation source, the plurality of position sensitive detectors each having a devoted channel set therefore, and being arranged in a circularly fashion around the radiation source, a signal amplifying unit which receives signals indicative of energy magnitude and location of the radiation source from the image measuring unit and amplifies the received signals into an electric signal, a mode selecting unit which receives the electric signal generated at the signal amplifying unit, and categorizes coincidence mode, single tracking mode of dual gamma ray, coincidence mode/gamma ray tracking mode, and coincidence dual gamma ray tracking mode according to the energy magnitude and the location and outputs a corresponding mode signal, a data storage unit which stores the signals indicative of the energy magnitude, time of radiation generation, and location of the radiation source, and the signal received from the mode selecting unit as a series of items, a data converting unit which converts the data stored at the data storage unit into interactive data, an image reconstructing unit which reconstructs the converted data into the 3D distribution image, and a display unit which displays the 3D distribution image received from the reconstructing unit.

In one embodiment, a method for processing a three dimensional (3D) distribution image may be provided, which may include preparing a plurality of position sensitive detectors to measure a radiation source, setting dedicated channels for the position sensitive detectors respectively, and measuring a gamma ray at an image measuring unit in which the plurality of position sensitive detectors is arranged in a circular fashion around the radiation source (step 1), receiving signals, indicative of an energy magnitude, travel time, and location of the radiation source where the radiation is generated, from the image measuring unit and amplifying the received signals at a signal amplifying unit (step 2), storing image data, amplified at the signal amplifying unit, at a data storage unit as a series of items (step 3), converting the image data into interactive data at a data converting unit, using the signals received from the signal amplifying unit (step 4), reconstructing the converted data at an image reconstructing unit into the 3D distribution image (step 5), and displaying the 3D distribution image received from the image reconstructing unit through a display unit (step 6).

According to an embodiment of the present invention, background events that deteriorate detection efficiency and image resolution are efficiently reduced, so that a 3D distribution image of radiation source can be acquired with improved image resolution. Additionally, since detection efficiency increases, patients or living organisms can have inspection within a shortened period of measuring time.

BRIEF DESCRIPTION OF THE DRAWINGS

The above and/or other aspects of what is described herein will be more apparent by describing certain exemplary embodiments with reference to the accompanying drawings, in which:

FIGS. 3A to 3D are views illustrating the detection mode implementable at the image measuring unit of FIG. 1, in which FIG. 3A illustrates coincidence mode, FIG. 3B illustrates single tracking mode of dual gamma rays, FIG. 3C illustrates coincidence mode/gamma ray tracking mode, and FIG. 3D illustrates coincidence tracking mode of dual gamma ray; and FIG. 4 is a flowchart provided to explain a method for processing a 3D distribution image of radiation source, according to an embodiment.

DETAILED DESCRIPTION OF EXEMPLARY EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical spirit of the present invention, based on the principle that the inventors can appropriately define the concepts of the terms to best describe their own invention. Also, it should be understood that detailed descriptions of well-known functions and structures related to the present invention will be omitted so as not to unnecessarily obscure the important point of the present invention.

Throughout the disclosure, the expression that a specific element "comprises" a specific constituent intends to mean that the specific element includes the specific constituent and others, and does not confer the meaning that the specific element exclusively includes the specific constituent. Further, the term "unit" or "portion" used throughout the disclosure corresponds to a unit that can process at least one function or operation, and that can be implemented as hardware, software, or a combination of hardware and software.

The present invention will now be described in further detail by examples. It would be obvious to those skilled in the art that these examples are intended to be more concretely illustrative and the scope of the present invention as set forth in the appended claims is not limited to or by the examples.

Figure 1:
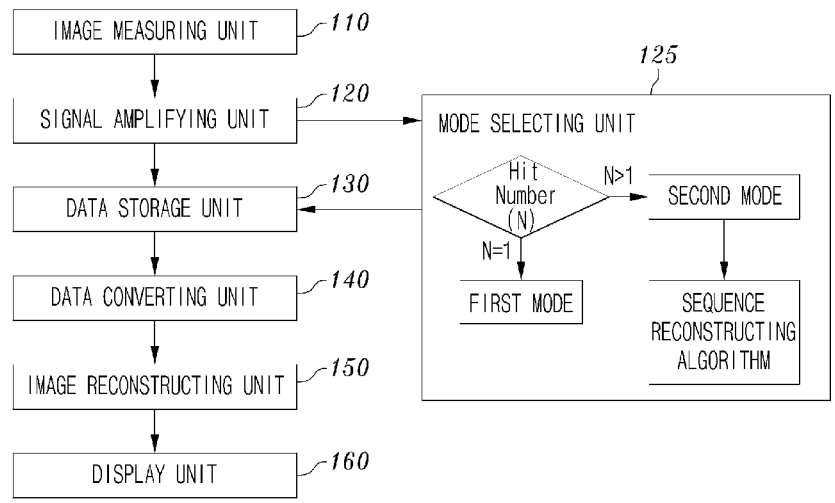
FIG. 1 is a block diagram of a system for processing a three-dimensional (3D) distribution image of a radiation source, according to an embodiment.

FIG. 1 is a block diagram of a system for processing a 3D distribution image of radiation source according to an embodiment.

Referring to FIG. 1, the system 100 for processing a 3D distribution image of radiation source according to an embodiment may include an image measuring unit 110, a signal amplifying unit 120, a data storage unit 130, a mode selecting unit 125, a data converting unit 140, an image reconstructing unit 150 and a display unit 160.

The image measuring unit 110 may include a plurality of position-sensitive detectors to measure the radiation source, in which devoted channels are set respectively. The plurality of position sensitive detectors is arranged in a circular fashion around the radiation source.

The signal amplifying unit 120 may receive from the image measuring unit 110 signals indicating a magnitude of energy of the radiation source, travel time, and a location of the radiation source where the radiation is generated, and amplify the received signals by converting the received signals into electric signals.

The mode selecting unit 125 may receive the electric signals generated at the signal amplifying unit 120, and select one mode from among the detection modes including, for example, coincidence mode, single tracking mode of dual gamma rays, coincidence mode/gamma ray tracking mode, and coincidence tracking mode of dual gamma rays, depending on the size of the electric signals and location, and outputs a mode signal according to the selection. Herein, the mode selecting unit 125 may output a mode signal by incorporating two or more modes.

Referring to FIG. 3A illustrating the coincidence mode, positrons of positron emitting radionuclides are absorbed into the matter, generating a pair of 511 keV gamma rays so that the generated gamma rays are emitted concurrently to opposite directions to conserve kinetic energy. The emitted gamma rays reach a predetermined detecting unit in N×M size and generate signals. The measuring units on two opposite ends notify the arrival of signal, and the radiation source is present on a straight line that connects these two measuring units. Since a plurality of gamma-ray pairs are generated, the source may be determined by connecting the measuring units that generate signals concurrently in straight lines respectively.

Referring to FIG. 3B which illustrates the single tracking mode of dual gamma rays, since the generated radiation pairs have high magnitude of energy, these secondarily interact with electrons with Compton and photoelectric effects to generate radiation scattering. The possibility is high that one out of the concurrently-generated radiations is measured. Accordingly, by tracking a secondary location of electron due to one of two radiations, location of the radiation is identified.

Referring to FIG. 3C which illustrates the coincidence mode/gamma ray tracking mode, while the radiation source generates a pair of radiations, part of the radiation source may generate separate radiation. The separate radiation interacts secondarily with the matters at the measuring units with Compton and photoelectric effects to thus generate radiation scattering with electron. The location of the radiation source is identified by tracking the secondary location of the electron due to radiations.

Referring to FIG. 3D which illustrates coincidence tracking mode of dual gamma rays, the location of the radiation source is identified by concurrently tracking the secondary location due to the pair of concurrently-generated radiations.

The data storage unit 130 may receive signals, indicated of the energy magnitude of the radiation source and the location of the radiation source where the radiation is generated, from the signal amplifying unit 120, and also receive a mode signal transmitted from the mode selecting unit 125, and database and store the received signals as predetermined items.

The data converting unit 140 may convert the data stored in the data storage unit 130 into interactive data.

The image reconstructing unit 150 may reconstruct the interactive data into a 3D distribution image.

The display unit 160 may receive the 3D distribution image from the image reconstructing unit 150 and display the resultant image.

Figure 2:
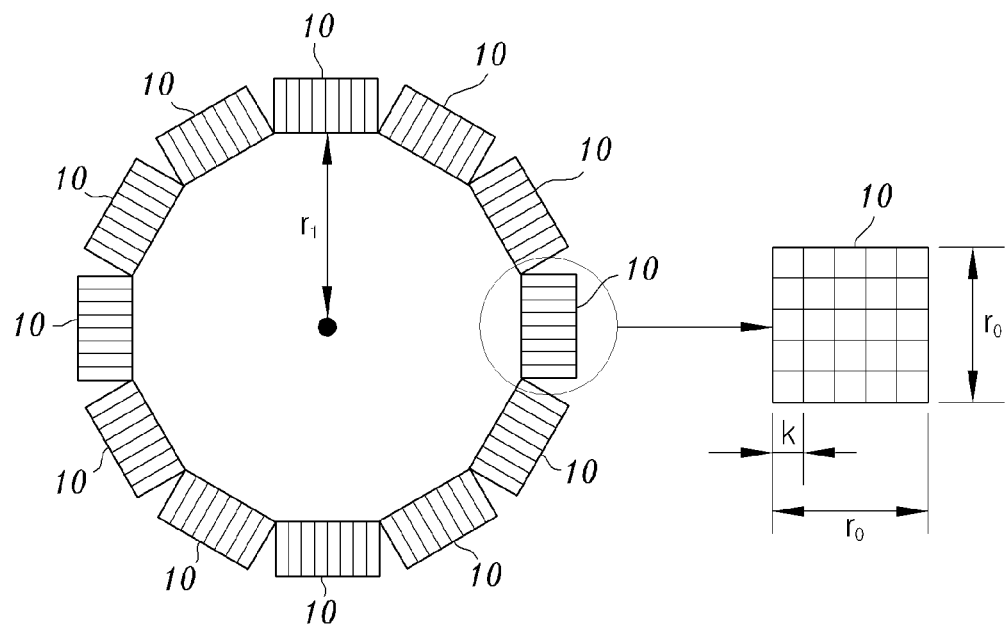
FIG. 2 is a view illustrating in detail the image measuring unit of FIG. 1.

FIG. 2 is a view illustrating the image measuring unit of FIG. 1 according to an embodiment.

Referring to FIG. 2, the image measuring unit 110 may include the plurality of position sensitive detectors 10 in N×M size (N, M=natural number). The position sensitive detectors 10 may respectively include different channels from each other and detect the location and energy magnitude of the radiation source (e.g., source of gamma ray, beta ray, or the like).

The position sensitive detectors 10 may each be formed in square shape (e.g., width, height=$r_o$), and include a plurality of signal electrodes (width, height=k).

FIGS. 3A to 3D are views illustrating the detection mode implementable at the image measuring unit of FIG. 1, in which FIG. 3A illustrates coincidence mode, FIG. 3B illustrates single tracking mode of dual gamma rays, FIG. 3C illustrates coincidence mode/gamma ray tracking mode, and FIG. 3D illustrates coincidence tracking mode of dual gamma rays.

FIG. 3A illustrates the coincidence mode, in which positrons of positron emitting radionuclides are absorbed into the matter, generating a pair of 511 keV gamma rays so that the generated gamma rays are emitted concurrently to opposite directions to conserve kinetic energy.

The emitted gamma rays reach a predetermined detecting unit in N×M size (e.g., position sensitive detectors) and generate signals. The measuring units (e.g., position sensitive detectors) on two opposite ends notify the arrival of signal, and the radiation source is present on a straight line that connects these two measuring units.

Since a plurality of gamma-ray pairs are generated, the source may be determined by connecting the measuring units that generate signals concurrently in straight lines respectively.

FIG. 3B illustrates the single tracking mode of dual gamma rays. Since the generated radiation pairs have high magnitude of energy, these secondarily interact with electrons with Compton and photoelectric effects to generate radiation scattering.

The possibility is high that one out of the concurrently-generated radiations is measured. Accordingly, by tracking a secondary location of electron due to one of two radiations, location of the radiation is identified.

FIG. 3C illustrates the coincidence mode/gamma ray tracking mode. While the radiation source generates a pair of radiations, part of the radiation source may generate separate radiation.

The separate radiation interacts secondarily with the matters at the measuring units with Compton and photoelectric effects to thus generate radiation scattering with electron. The location of the radiation source is identified by tracking the secondary location of the electron due to radiations.

FIG. 3D illustrates coincidence tracking of dual gamma rays, in which the location of the radiation source is identified by concurrently tracking the secondary location due to the pair of concurrently-generated radiations.

FIG. 4 is a flowchart provided to explain a method for processing 3D distribution image of radiation source according to an embodiment.

Referring to FIG. 4, the method for processing 3D distribution image of radiation source may include the following steps (S10 to S60).

In the first step (S10), a plurality of position sensitive detectors is provided to measure the radiation source, devoted channels are set for the respective detectors, and the image measuring unit 110, in which the plurality of position sensitive detectors is arranged in a circular fashion, measures the radiation source.

In the second step (S20), signals, indicative of the energy magnitude and location of the radiation source where the radiation is generated, are received and amplified at the signal amplifying unit 120.

In the third step (S30), the amplified image data from the signal amplifying unit 120 is stored at the data storage unit 130.

In the fourth step (S40), the image data is converted into interactive data at the data converting unit 140 using the signal received from the signal amplifying unit 120.

In the fifth step (S50), the converted data is reconstructed into 3D distribution image at the image reconstructing unit 150.

In the sixth step (S60), the 3D distribution image received from the image reconstructing unit 150 is displayed through the display unit 160.

According to an embodiment of the present invention, background events that deteriorate sensitivity and image resolution are efficiently reduced, so that a 3D distribution image of radiation source can be acquired with improved image resolution. Additionally, since sensitivity increases, patients or living organisms can have diagnostic examination within a shortened period of time.

The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

What is claimed is:

1. A system for processing three dimensional (3D) distribution image of a radiation source, comprising:
    an image measuring unit which comprises a plurality of position sensitive detectors to measure the radiation source, the plurality of position sensitive detectors each having a devoted channel set therefore, and being arranged in a circularly fashion around the radiation source;
    a signal amplifying unit which receives signals indicative of energy magnitude and location of the radiation source from the image measuring unit and amplifies the received signals into an electric signal;
    a mode selecting unit which receives the electric signal generated at the signal amplifying unit, and selects a detection mode according to the energy magnitude and the location and outputs a corresponding mode signal;
    a data storage unit which stores the signals indicative of the energy magnitude, time of radiation generation, and location of the radiation source, and the signal received from the mode selecting unit as a series of items;
    a data converting unit which converts the data stored at the data storage unit into interactive data;
    an image reconstructing unit which reconstructs the converted data into the 3D distribution image; and
    a display unit which displays the 3D distribution image received from the reconstructing unit.

2. The system according to claim 1, wherein the image measuring unit comprises the plurality of position sensitive detectors in N×M size (N, M =natural number), and the plurality of position sensitive detectors each detect the location of the radiation source, travel time and energy magnitude of the radiation through channels different from each other.

3. The system according to claim 2, wherein the plurality of position sensitive detectors each comprise a plurality of signal electrodes of a predetermined shape with width (k) and height (k).

4. The system according to claim 1, wherein the mode selecting unit categorizes the electric signal received along the respective channels to under coincidence mode.

5. The system according to claim 1, wherein the mode selecting unit categorizes the electric signal received along the respective channels to under single tracking mode of dual gamma ray.

6. The system according to claim 1, wherein the mode selecting unit categorizes the electric signal received along the respective channels to under coincidence mode/gamma ray tracking mode.

7. The system according to claim 1, wherein the mode selecting unit categorizes the electric signal received along the respective channels to under coincidence dual gamma ray tracking mode.

8. The system according to claim 1, wherein the mode selecting unit implements the coincidence mode, single tracking mode of dual gamma rays, coincidence mode/ gamma ray tracking mode, and coincidence dual gamma ray tracking mode, depending on the electric signal received through the respective channels.

9. A system for processing three dimensional (3D) distribution image of a radiation source, comprising:
    an image measuring unit which comprises a plurality of position sensitive detectors to measure the radiation source, the plurality of position sensitive detectors each having a devoted channel set therefore, and being arranged in a circularly fashion around the radiation source;
    a signal amplifying unit which receives signals indicative of energy magnitude and location of the radiation source from the image measuring unit and amplifies the received signals into an electric signal;
    a mode selecting unit which receives the electric signal generated at the signal amplifying unit, and categorizes coincidence mode, single tracking mode of dual gamma ray, coincidence mode/gamma ray tracking mode, and coincidence dual gamma ray tracking mode according to the energy magnitude and the location and outputs a corresponding mode signal;
    a data storage unit which stores the signals indicative of the energy magnitude, time of radiation generation, and location of the radiation source, and the signal received from the mode selecting unit as a series of items;
    a data converting unit which converts the data stored at the data storage unit into interactive data;
    an image reconstructing unit which reconstructs the converted data into the 3D distribution image; and
    a display unit which displays the 3D distribution image received from the reconstructing unit.

10. A method for processing a three dimensional (3D) distribution image, comprising:
    preparing a plurality of position sensitive detectors to measure a radiation source, setting dedicated channels for the position sensitive detectors respectively, and measuring a gamma ray at an image measuring unit in which the plurality of position sensitive detectors is arranged in a circular fashion around the radiation source;
    receiving signals, indicative of an energy magnitude, travel time, and location of the radiation source where the radiation is generated, from the image measuring unit and amplifying the received signals at a signal amplifying unit;
    receiving amplified signals from the signal amplifying unit at a mode selecting unit and outputting a corresponding mode signal;
    storing the mode signal from the mode selecting unit and, amplified signals from the signal amplifying unit at a data storage unit as a series of items;
    converting the data stored at the data storage unit into interactive data at a data converting unit;
    reconstructing the converted data at an image reconstructing unit into the 3D distribution image; and
    displaying the 3D distribution image received from the image reconstructing unit through a display unit.

* * * * *